United States Patent
Flockerzi et al.

(10) Patent No.: US 7,470,704 B2
(45) Date of Patent: Dec. 30, 2008

(54) BENZONAPHTHYRIDINES

(75) Inventors: Dieter Flockerzi, Allensbach (DE); Rolf-Peter Hummel, Radolfzell (DE); Felix Reutter, Constance (DE)

(73) Assignee: Nycomed GmbH, Constance (DE)

( * ) Notice: Subject to any disclaimer, the term of this patent is extended or adjusted under 35 U.S.C. 154(b) by 228 days.

(21) Appl. No.: 10/525,566

(22) PCT Filed: Aug. 29, 2003

(86) PCT No.: PCT/EP03/09617

§ 371 (c)(1), (2), (4) Date: Feb. 25, 2005

(87) PCT Pub. No.: WO2004/022557

PCT Pub. Date: Mar. 18, 2004

(65) Prior Publication Data

US 2006/0167034 A1    Jul. 27, 2006

Related U.S. Application Data

(60) Provisional application No. 60/407,689, filed on Sep. 4, 2002.

(30) Foreign Application Priority Data

Sep. 4, 2002    (EP) .................... 02019904

(51) Int. Cl.
*A61K 31/4375* (2006.01)
*C07D 401/04* (2006.01)

(52) U.S. Cl. ........................ 514/292; 546/81

(58) Field of Classification Search ............. 546/81; 514/292
See application file for complete search history.

(56) References Cited

U.S. PATENT DOCUMENTS

| | | | |
|---|---|---|---|
| 6,008,215 A | 12/1999 | Flockerzi | |
| 6,143,759 A | 11/2000 | Flockerzi | |
| 6,306,869 B1 | 10/2001 | Flockerzi | |
| 6,436,952 B1 | 8/2002 | Flockerzi | |

2004/0097537 A1    5/2004    Flockerzi

FOREIGN PATENT DOCUMENTS

| | | |
|---|---|---|
| WO | 98/21208 A1 | 5/1998 |
| WO | 98/40382 A1 | 9/1998 |
| WO | 99/57118 A1 | 11/1999 |
| WO | 00/12501 | 3/2000 |
| WO | 02/066476 A1 | 8/2002 |
| WO | 2004/018465 A2 | 3/2004 |

OTHER PUBLICATIONS

Montana et al., "Phosphodiesterase 4 inhibitors", *Annual Reports in Medicinal Chemistry*, (2001), 36, chapter 5.

Souness et al. "Immunosuppressive and anti-inflammatory effects of cyclic AMP phosphodiesterase (PDE) type 4 inhibitors", *Immunopharmacology*, 47 (2000), pp. 127-162.

*Primary Examiner*—Rita J Desai
(74) *Attorney, Agent, or Firm*—Nath Law Group; Joshua B. Goldberg; Sheldon M. McGee

(57)    ABSTRACT

The compounds of formula I

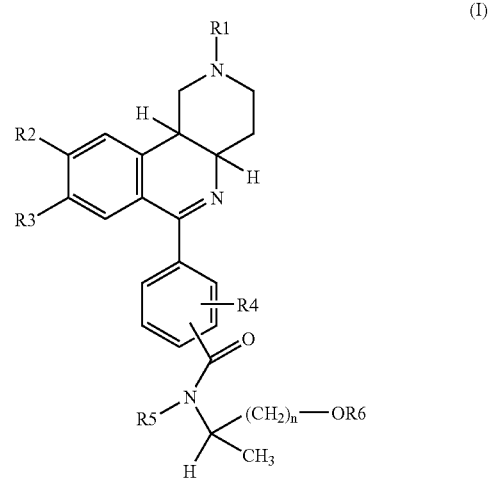

in which R1, R2, R3, R4, R5, R6 and n have the meanings as indicated in the description, are novel effective PDE3/4 inhibitors.

7 Claims, No Drawings

BENZONAPHTHYRIDINES

FIELD OF APPLICATION OF THE INVENTION

The invention relates to novel 6-phenylbenzonaphthyridines which are used in the pharmaceutical industry for the production of pharmaceutical compositions.

KNOWN TECHNICAL BACKGROUND

The international applications WO98/21208 (=U.S. Pat. No. 6,008,215), WO98/40382 (=U.S. Pat. No. 6,143,759), WO99/57118 (=U.S. Pat. No. 6,306,869), W00/12501 and WO02/066476 describe 6-phenylbenzonaphthyridines and their N-oxides as PDE3/4 inhibitors.

DESCRIPTION OF THE INVENTION

It has now been found that the compounds of formula 1, which are described in more detail below and which differ from the prior-art compounds in particular by substitution on the 6-phenyl ring, have surprising and particularly advantageous properties.

The invention thus relates to compounds of formula 1,

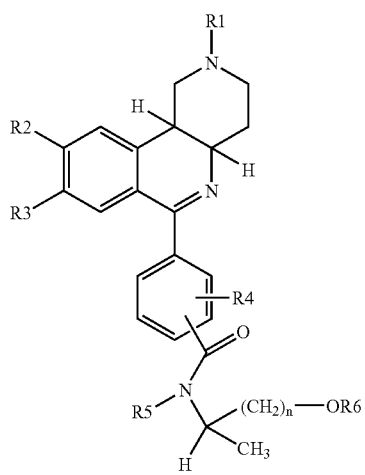

(1)

in which

R1 is 1-4C-alkyl,

R2 is hydroxyl, 1-4C-alkoxy, 3-7C-cycloalkoxy, 3-7C-cycloalkylmethoxy, or 1-4C-alkoxy which is completely or predominantly substituted by fluorine, R3 is hydroxyl, 1-4C-alkoxy, 3-7C-cycloalkoxy, 3-7C-cycloalkylmethoxy, or 1-4C-alkoxy which is completely or predominantly substituted by fluorine, or in which R2 and R3 together are a 1-2C-alkylenedioxy group, R4 is hydrogen, halogen, nitro, 1-4C-alkyl, trifluoromethyl or 1-4C-alkoxy, R5 is hydrogen or 1-8C-alkyl, R6 is hydrogen, 1-8C-alkylcarbonyl, 3-7C-cycloalkylcarbonyl, 3-7C-cycloalkylmethylcarbonyl, Arylcarbonyl or Aryl-1-4C-alkylcarbonyl bedeutet, Aryl is phenyl or phenyl substituted by R7 and/or R8, R7 is halogen, nitro, 1-4C-alkyl or 1-4C-alkoxy, R8 is halogen, nitro, 1-4C-alkyl or 1-4C-alkoxy, n is 1 or 2, the salts, the N-oxides of these compounds and the salts of the latter.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3-7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1-4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned. In this context, "predominantly" means that more than half of the hydrogen atoms of the 1-4C-alkoxy groups are replaced by fluorine atoms.

1-2C-Alkylenedioxy represents, for example, the methylenedioxy(—O—CH$_2$—O—) or the ethylenedioxy(—O—CH$_2$—CH$_2$—O—) radical.

Halogen within the meaning of the invention is fluorine, chlorine or bromine.

1-8C-Alkyl represents straight-chain or branched alkyl radicals having 1 to 8 carbon atoms. Examples which may be mentioned are the octyl, heptyl, isoheptyl(5-methylhexyl), hexyl, isohexyl(4-methylpentyl), neohexyl(3,3-dimethylbutyl), pentyl, isopentyl(3-methylbutyl), neopentyl(2,2-dimethylpropyl), butyl, isobutyl, sec-butyl, tert-butyl, propyl, isopropyl, ethyl or methyl radical.

1-8C-Alkylcarbonyl is a carbonyl group to which one of the abovementioned 1-8C-alkyl radicals is bonded. An example is the acetyl radical [CH$_3$C(O)—].

3-7C-Cycloalkyl represents the cyclopropyl, cyclobutyl, cyclopentyl, cyclohexyl or cycloheptyl radical.

3-7C-Cycloalkylmethyl represents a methyl radical which is substituted by one of the abovementioned 3-7C-cycloalkyl radicals. Examples which may be mentioned are the cycloalkylmethyl radicals cyclopropylmethyl, cyclobutylmethyl and cyclopentylmethyl.

3-7C-Cycloalkylcarbonyl is a carbonyl group to which one of the above-mentioned 3-7C-cycloalkyl radicals is bonded. An example is the cyclopentylcarbonyl radical.

3-7C-Cycloalkylmethylcarbonyl is a carbonyl group to which one of the above-mentioned 3-7C-cycloalkylmethyl radicals is bonded. An example is the cyclopropylmethylcarbonyl radical.

"N-oxides of these compounds" stands for any single or multiple N-oxide(s), which can be formed starting from the compounds of formula 1. Preferred are the single N-oxides at the nitrogen atom in 2-position of the benzonaphthyridine ring system.

The substituents R4 and —C(O)N(R5)—CH(CH₃)—(CH₂)ₙ—OR6 of the compounds of formula 1 can be attached in the ortho, meta or para position with respect to the binding position in which the 6-phenyl ring is bonded to the benzonaphthyridine ring system. Preference is given to compounds of formula 1, in which R4 is hydrogen and —C(O)N(R5)—CH(CH₃)—(CH₂)ₙ—OR6 is attached in the meta or in the para position; most preferred is the para position.

Suitable salts of compounds of formula 1—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, 2-hydroxy-succinic acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand salts with bases are also suitable. Examples of salts with bases which may be mentioned are alkali metal (lithium, sodium, potassium) or calcium, aluminum, magnesium or titanium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

It is known to the person skilled in the art that the compounds according to the invention and their salts, for example when they are isolated in crystalline form, may comprise varying amounts of solvents. Accordingly, the invention also embraces all solvates and in particular all hydrates of the compounds of formula 1, and also all solvates and in particular all hydrates of the salts of the compounds of formula 1.

Compounds of formula 1 to be emphasized are those in which
R1 is 1-4C-alkyl,
R2 is 1-4C-alkoxy, 3-6C-cycloalkoxy, 3-6C-cycloalkylmethoxy, or 1-4C-alkoxy which is completely or predominantly substituted by fluorine,
R3 is 1-4C-alkoxy, 3-6C-cycloalkoxy, 3-6C-cycloalkylmethoxy, or 1-4C-alkoxy which is completely or predominantly substituted by fluorine,
R4 is hydrogen, 1-4C-alkyl, trifluoromethyl or 1-4C-alkoxy,
R5 is hydrogen or 1-4C-alkyl,
R6 is hydrogen, 1-4C-alkylcarbonyl, 3-7C-cycloalkylcarbonyl, 3-7C-cycloalkylmethylcarbonyl, Arylcarbonyl or Aryl-1-2C-alkylcarbonyl,
Aryl is phenyl or phenyl substituted by R7 and/or R8,
R7 is halogen, nitro, 1-4C-alkyl or 1-4C-alkoxy,
R8 is halogen, nitro, 1-4C-alkyl or 1-4C-alkoxy,
n is 1 or 2,
the salts, the N-oxides of these compounds and the salts of the latter.

Compounds of formula I to be particularly emphasized are those in which
R1 is methyl,
R2 is 1-4C-alkoxy,
R3 is 1-4C-alkoxy,
R4 is hydrogen,
R5 is 1-4C-alkyl,
R6 is hydrogen, 1-4C-alkylcarbonyl, Arylcarbonyl or Aryl-1-2C-alkylcarbonyl,
Aryl is phenyl or phenyl substituted by R7 and/or R8,
R7 is nitro, 1-2C-alkyl or 1-2C-alkoxy,
R8 is 1-2C-alkoxy,
n is 1 or 2,
the salts, the N-oxides of these compounds and the salts of the latter.

Preferred compounds of formula 1 are those in which
R1 is methyl,
R2 is methoxy or ethoxy,
R3 is methoxy,
R4 is hydrogen,
R5 is isopropyl,
and in which either
R6 is hydrogen, phenylcarbonyl, benzylcarbonyl, 4-nitrophenylcarbonyl, 3,4-dimethoxyphenylcarbonyl, 3,5-dimethoxyphenylcarbonyl or acetyl and
n is 1,
or
R6 is phenylcarbonyl, benzylcarbonyl or 3,4-dimethoxybenzylcarbonyl and
n is 2,
the salts, the N-oxides of these compounds and the salts of the latter.

Particularly preferred compounds of formula 1 are Phenylacetic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}isopropyl-amino)-propyl ester, Benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester, 3,4-Dimethoxy-benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester, 3,5-Dimethoxy-benzoic acid (S)-2-({1-[4-((4aR,10bS)-9-ethoxy-8-methoxy-2-methyl-1,2,3,4,4a,10b-hexahydro-benzo[c][1,6]naphthyridin-yl)-phenyl]-methanoyl}-isopropyl-amino)-propyl ester, Acetic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester, Benzoic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester, Phenyl-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester, (3,4-Dimethoxy-phenyl)-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)- butyl ester, 4-Nitro-benzoic acid (S)-2-({1-[4-((4aR,10bS)-9-ethoxy-8-methoxy-2-methyl-1,2,3,4,4a,10b-hexahydro-benzo[c][1,6]naphthyridin-yl)-phenyl]-methanoyl}-isopropyl-amino)-propyl ester, 4-Nitro-benzoic acid (R)-2-({1-[4-(4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester, 4-((4aR,10bS)-9-Ethoxy-8-methoxy-2-methyl-1,2,3,4,4a,10b-hexahydro-benzo[c][1,6]naphthyridin-6-yl)-N-((S)-2-hydroxy-1-methyl-ethyl)-N-isopropyl-benzamide, 4-((4aR,10bS)-9-Ethoxy8-methoxy-2-methyl-1,2,3,4,4a,10b-hexahydro-benzo[c][1,6]naphthyridin-6-yl)-N-((R)-2-hydroxy-1-methyl-ethyl)-N-isopropyl-benzamide, as well as the salts, the N-oxides of these compounds and the salts of the latter.

A special embodiment of the compounds of the present invention include those compounds of formula 1, in which R1 is methyl, R2 is ethoxy and R3 is methoxy.

Another special embodiment of the compounds of the present invention include those compounds of formula 1 in which R1 is methyl, R2 is ethoxy, R3 is methoxy and R4 is hydrogen.

Still another special embodiment of the compounds of the present invention include those compounds of formula 1 in which R1 is methyl, R2 is ethoxy, R3 is methoxy, R4 is hydrogen and the radical —C(O)N(R5)—CH(CH$_3$)—(CH$_2$)$_n$—OR6 is attached to the 6-phenyl-ring in para-position.

The compounds of formula 1 are chiral compounds having chiral centers in positions 4a and 10b as well as in the radical —C(O)N(R5)—CH(CH$_3$)—(CH$_2$)$_n$—OR6

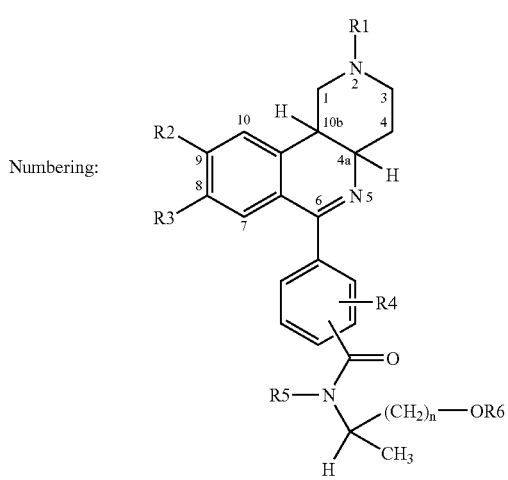

Numbering: (1)

The invention therefore includes all conceivable pure diastereomers and pure enantiomers and mixtures thereof in any mixing ratio, including the racemates. Preference is given to compounds of formula 1 in which the hydrogen atoms in positions 4a and 10b are in the cis position relative to one another. The pure cis enantiomers and their mixtures in any mixing ratio and including the racemates are particularly preferred.

The most preferred compounds in this context are those compounds of formula 1, which have with respect to the chiral centers the configuration shown in formulae (1*) and (1**):

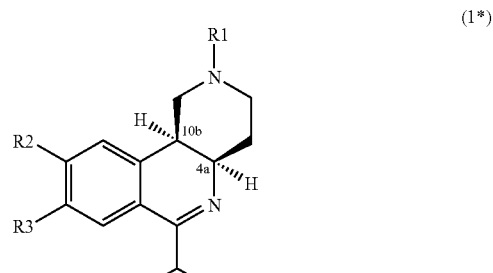

(1*)

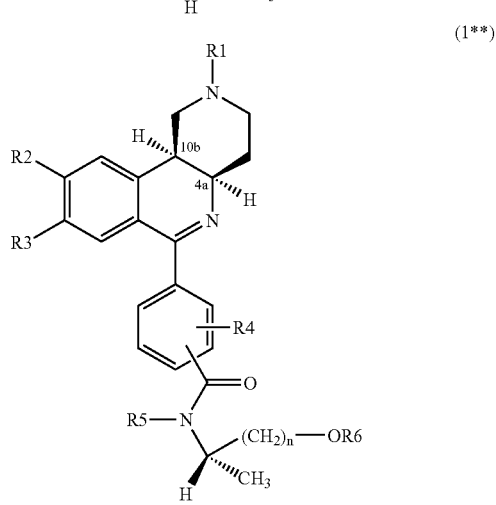

(1**)

The compounds according to the invention can be prepared, for example, as shown in the reaction scheme 1 below.

The compounds of formula 1 can be prepared by reacting compounds of formula 4, in which R1, R2, R3 and R4 have the meanings given above, with compounds of formula 2, in which R6 and n have the meanings given above.

Advantageously, the reaction is carried out using standard coupling reagents known to the person skilled in the art, such as, for example, N,N'-dicyclohexylcarbodiimide, N'-3-dimethylaminopropyl)-N-ethylcarbodiimide or O-Benzotriazol-1-yl-N,N,N',N'-bis-(tetramethylen)-uronium-hexafluorophosphat.

Alternatively, the compounds of formula 4, in which R1, R2, R3 and R4 have the meanings given above can in a first step be activated, for example by forming an acid halide or acid anhydride (compounds of formula 3; Y is for example halogen, preferably chlorine) and in a second step be reacted with compounds of formula 2, in which R6 and n have the meanings given above, to yield the compounds of formula 1.

Compounds of formula 1, in which R1, R2, R3, R4 and R5 have the meanings given above and R6 has the meaning hydrogen (H) preferably are not directly prepared by reacting compounds of formulae 3 or 4 with compounds of formula 2. They can be prepared starting from compounds of formula 1, in which R1, R2, R3, R4 and R5 have the meanings given above and R6 has a meaning other than hydrogen, by saponification of the —$CH_2$)$_n$—OR6 ester group by treating with strong bases like sodium, potassium or lithium hydroxide in water or organic solvents like alcohols, ethers, DMSO and DMF or preferably under mild saponification conditions by treating with weak bases in the mentioned solvents. Suitable reaction conditions for the saponification step are described, for example, in the following examples.

Compounds of formula 2 are known or can be prepared according to processes known to the person skilled in the art or as described in the following examples.

The preparation of compounds of formulae 3 and 4 is described, for example, in the International Patent Applications WO98/21208 (=U.S. Pat. No. 6,008,215) and WO02/066476.

Compounds of formulae (1*) and (1**) can be prepared by reacting (4aR,10bS)-configurated compounds of formulae 3 or 4 with enantiomeric pure compounds of formula 2. The preparation of (4aR, 10bS)-configuurated compounds of formulae 3 and 4 is also described in the International Patent Applications WO98/21208 (=U.S. Pat. No. 6,008,215) and WO02/066476. The preparation of enantiomeric pure compounds of formula 2 is known to the person skilled in the art; they can be prepared, for example, starting from 2R-amino-propanol, 2S-amino-propanol, 3R-amino-butanol or 3S-amino-butanol or as described in Tetrahedron Vol. 45, No. 16, pp. 4969 to 4988, 1989.

Reaction scheme 1:

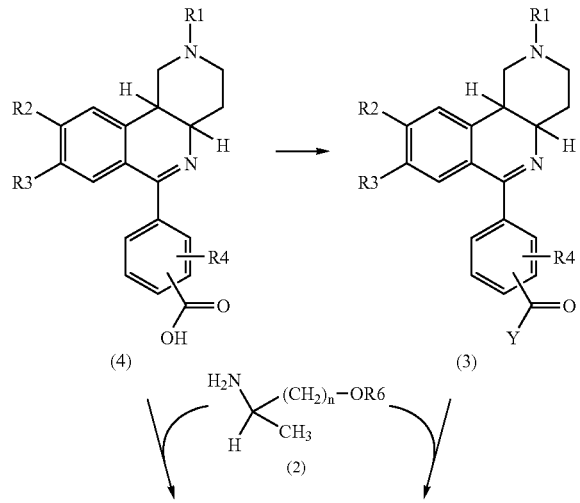

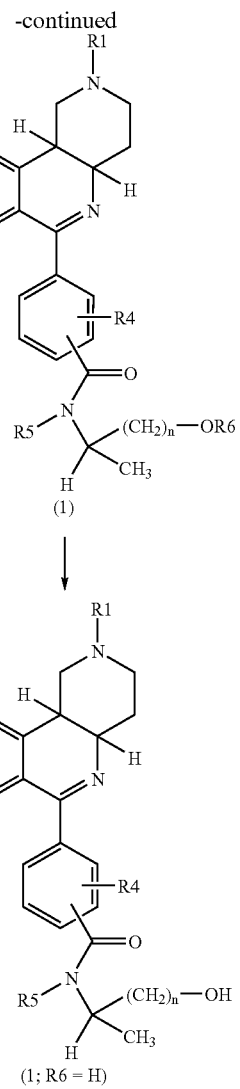

The compounds of formula 1 prepared by the processes described above can, if desired, be converted into their salts, or salts of the compounds of formula 1 obtained can, if desired, be converted into the free compounds. Corresponding processes are known to the person skilled in the art.

In addition, the compounds of formula 1 can be converted by derivatisation into further compounds of formula 1. Thus, for example, compounds of formula 1 can be converted, if desired, into their N-oxides.

The N-oxidation is carried out in a manner, which is known to the person skilled in the art, for example with the aid of hydrogen peroxide in methanol or with the aid of m-chloroperoxybenzoic acid in dichloromethane. The person skilled in the art is familiar on the basis of his/her expert knowledge with the reaction conditions, which are specifically necessary for carrying out the N-oxidation.

It is also known to the person skilled in the art that, if a plurality of reactive centers are present in a starting material or intermediate, it may be necessary to temporarily block one or more reactive centers with protective groups so that a reaction takes place only at the desired reactive center. A detailed description of how to use a large number of proven protective groups can be found, for example, in T. W. Greene, Protective Groups in Organic Synthesis, John Wiley & Sons, 1991.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into Pharmacologically acceptable salts.

The following examples serve to illustrate the invention in greater detail without restricting it. Further compounds of formula 1, whose preparation is not explicitly described, can also be prepared in an analogous manner or in a manner familiar per se to the person skilled in the art using customary process techniques.

In the examples, m.p. stands for melting point, h for hour(s), RT for room temperature, calc for calculated and fnd for found. The compounds mentioned in the examples and their salts are preferred subject of the invention.

EXAMPLES

End Products

1. Phenyl-acetic acid (S)-2-({1-[4-((4aR,10bS-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester

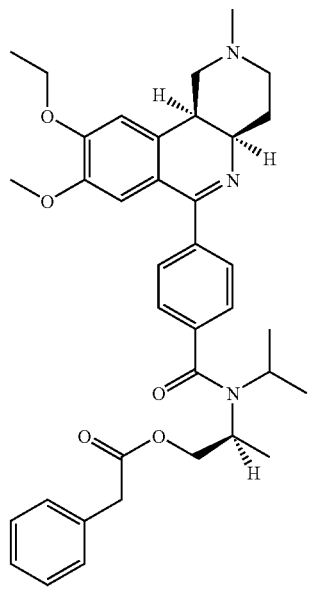

0.9 ml of Diisopropyl amine are added to a suspension of 1.0 g 4-((4aR,10bS)-9-ethoxy-8-methoxy-2-methyl-1,2,3,4,4a,10b-hexahydrobenzo[c][1,6]naphthyridin-6-yl)benzoic acid in 50 ml of acetonitrile. The reaction mixture is stirred at RT for 30 min and then 1.0 g of O-Benzotriazol-1-yl-N,N,N',N'-bis-(tetrame-thylen)-uronium-hexafluorophosphate (HBTU) are added, yielding a clear light-brown solution. This solution is added to a solution of 0.81 g of phenyl-acetic acid (S)-2-isopropylamino-propyl ester hydrochloride in a mixture of 50 ml acetonitrile and 0.5 ml of di-isopropyl amine. The reaction mixture is stirred at RT for about 15 h and filtered. The filtrate is substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. This gives 0.73 g of the title compound as a solid foam.

MS: calc.: $C_{37} H_{45} N_3 O_5$ (611.79) fnd.: [M+1] 612.2

Analogously to example 1, the following title compounds are obtained when, instead of phenyl-acetic acid (S)-2-isopropylamino-propyl ester hydrochloride, the respective appropriately substituted ester are used as reaction partner:

2. Benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester

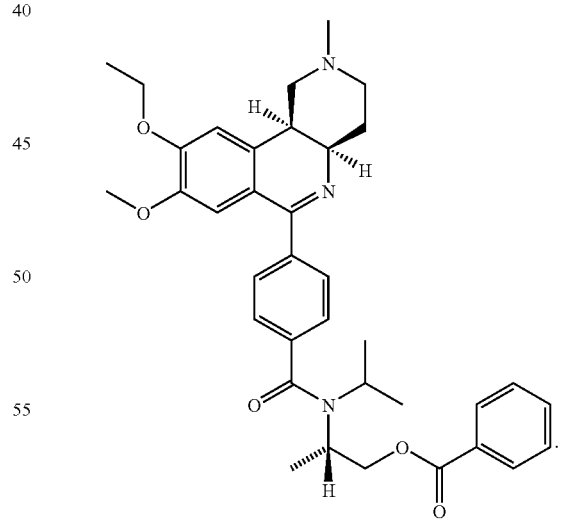

Prepared from 4-((4aR,10bS)-9-ethoxy-8-methoxy-2-methyl-1,2,3,4,4a,10b-hexahydrobenzo[c][1,6]-naphthyridin-6-yl)benzoic acid and benzoic acid (S)-2-isopropylamino-propyl ester as described for example 1.

MS: calc.: $C_{36} H_{43} N_3 O_5$ (597.75) fnd.: [M+1] 598.2

3. 3,4-Dimethoxy-benzoic acid(S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester

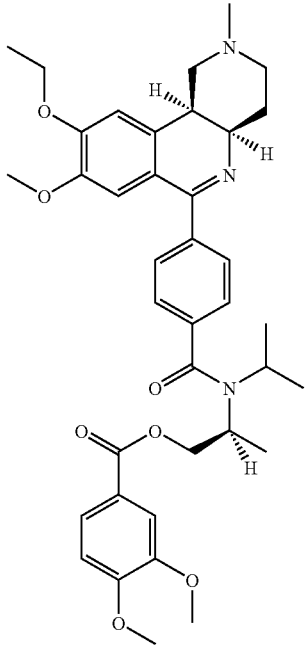

Prepared from 4-((4aR,10bS)-9-ethoxy-8-methoxy-2-methyl-1,2,3,4,4a,10b-hexahydrobenzo[c][1,6]-naphthyridin-6-yl)benzoic acid and 3,4-dimethoxy-benzoic acid (S)-2-isopropylamino-propyl ester as described for example 1.

MS: calc.: $C_{38} H_{47} N_3 O_7$ (657.81) fnd.: [M+1] 658.2

4. 3,5-Dimethoxy-benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester

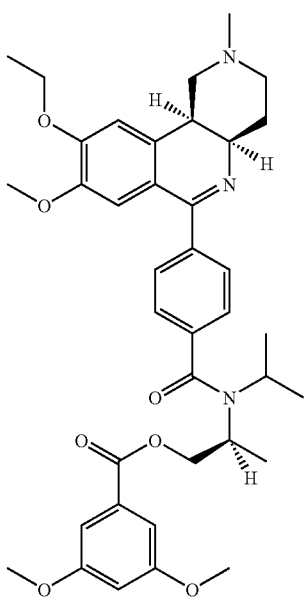

Prepared from 4-((4aR,10bS)-9ethoxy-8-methoxy-2-methyl-1,2,3,4,4a,10b-hexahydrobenzo[c][1,6]-naphthyridin-6-yl)benzoic acid and 3,5-dimethoxy-benzoic acid (S)2-isopropylamino-propyl ester as described for example 1.

MS: calc.: $C_{38} H_{47} N_3 O_7$ (657.81) fnd.: [M+1] 658.2

5. Acetic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester dihydrochloride

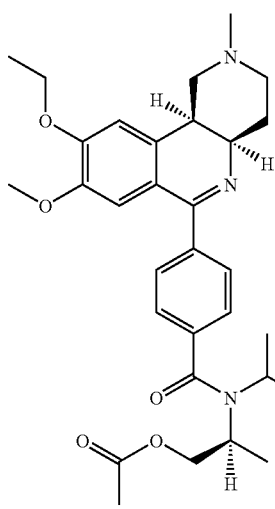

Prepared from 4-((4aR,10bS)-9-ethoxy-8-methoxy-2-methyl-1,2,3,4,4a,10b-hexahydrobenzo[c][1,6]-naphthyridin-6-yl)benzoic acid and acetic acid (S)-2-isopropylamino-propyl ester as described for example 1.

MS: calc.: $C_{31} H_{41} N_3 O_5$ (535.69) fnd.: [M+1] 536.3

6. Benzoic acid 3-({1-[4-((4aR,10bS)-9-ethoxy-8-methoxy-2-methyl-1,2,3,4,4a,10b-hexahydrobenzo[c][1,6]naphthyridin-6-yl)-phenyl]-methanoyl}-isopropyl-amino)-butyl ester

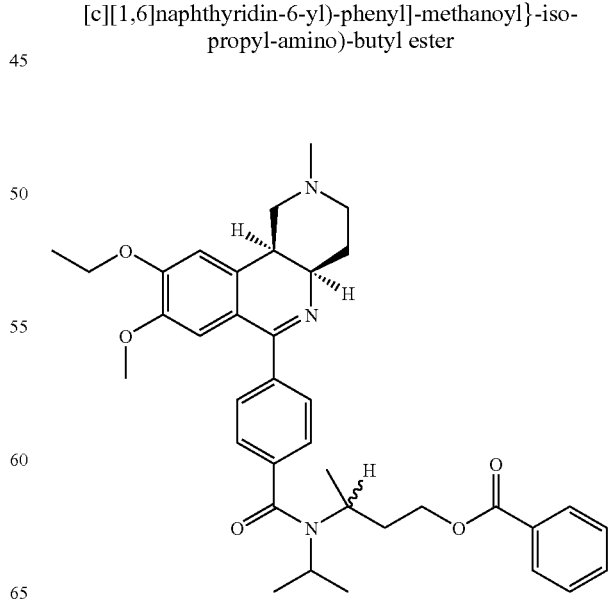

Prepared from 4-((4aR,10bS)-9-ethoxy-8-methoxy-2-methyl-1,2,3,4,4a,10b-hexahydrobenzo[c][1,6]-naphthyridin-6-yl)benzoic acid and rac-benzoic acid 3-isopropylamino-butyl ester as described for example 1.

MS: calc.: $C_{37} H_{45} N_3 O_5$ (611.79) fnd.: [M+1] 612.2

7. Phenyl-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester

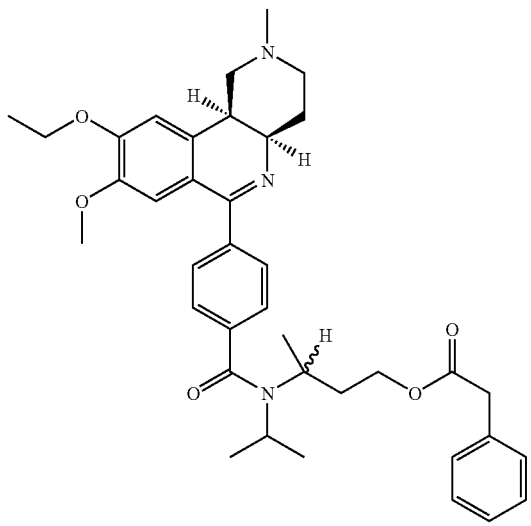

Prepared from 4-((4aR,10bS)-9-ethoxy-8-methoxy-2-methyl-1,2,3,4,4a,10b-hexahydrobenzo[c][1,6]-naphthyridin-6-yl)benzoic acid and rac-phenyl-acetic acid 3-isopropylamino-butyl ester as described for example 1.

MS: calc.: $C_{38} H_{47} N_3 O_5$ (625.82) fnd.: [M+1] 626.3

8. (3,4-Dimethoxy-phenyl)-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester

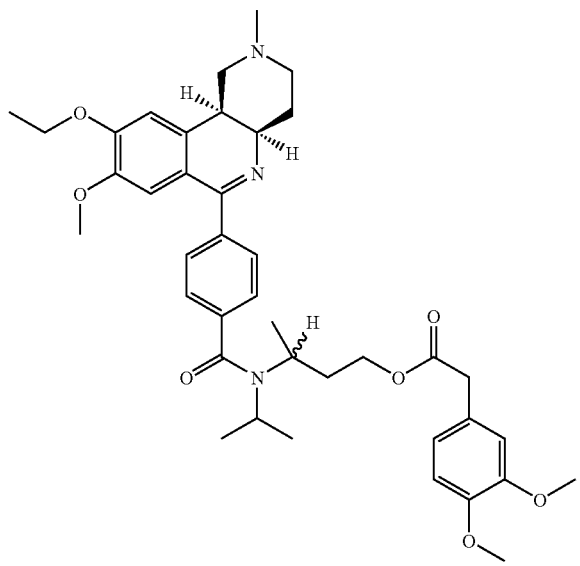

Prepared from 4-((4aR,10bS)-9-ethoxy-8-methoxy-2-methyl-1,2,3,4,4a,10b-exahydrobenzo[c][1,6]-naphthyridin-6-yl)benzoic acid and rac-3,4-dimethoxy-phenyl)-acetic acid 3-isopropylamino-butyl ester as described for example 1.

MS: calc.: $C_{40} H_{51} N_3 O_7$ ( 685.87) fnd.: [M+1] 686.4

9. 4-Nitro-benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester

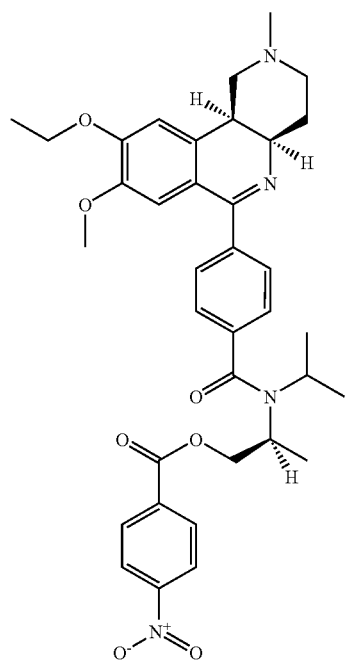

Over a period of about 5 min, a solution of 0.42 g of 4-((4aR,10bS)-9-ethoxy-8-methoxy-2-methyl-1,2,3,4,4a,10b-hexahydrobenzo[c][1,6]naphthyridin-6-yl)benzoyl chloride in 10 ml of acetonitrile is added dropwise to a mixture, cooled with ice/water, of 0.31 g of 4-nitro-benzoic acid (S)-2-isopropylamino-propyl ester hydrochloride and 0.5 g of triethylamine in 10 ml of acetonitrile. The reaction mixture is stirred at RT for about 15 h and then substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. This gives 0.34 g of the title compound as a solid foam.

MS: calc.: $C_{36} H_{42} N_4 O_7$ (642.76) fnd.: [M+1] 643.3

10. 4-Nitro-benzoic acid (R)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)propyl ester

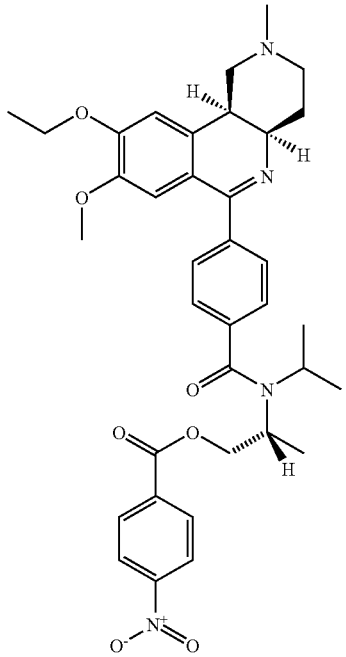

Prepared from 4-((4aR,10bS)-9-ethoxy-8-methoxy-2-methyl-1,2,3,4,4a,10b-hexahydrobenzo[c][1,6]-naphthyridin-6-yl)benzoyl chloride and 4-nitro-benzoic acid (R)-2-isopropylamino-propyl ester hydrochloride as described for example 9.

MS: calc.: $C_{36} H_{42} N_4 O_7$ (642.76) fnd.: [M+1] 643.3

11. 4-((4aR,10bS)-9-Ethoxy-8-methoxy-2-methyl-1,2,3,4,4a,10b-hexahydro-benzo[c][1,6]-naphthyridin-6-yl)-N-((S)-2-hydroxy-1-methyl-ethyl)-N-isopropyl-benzamide

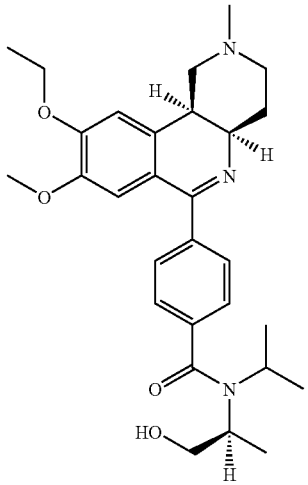

2 ml of triethylamine are added to a solution of 0.64 g of 4-Nitro-benzoic acid (S)-2-({1-[4-((4aR,10bS)-9-ethoxy-8-methoxy-2-methyl-1,2,3,4,4a,10b-hexahydro-benzo[c][1,6] naphthyridin-6-yl)-phenyl]-methanoyl}-isopropyl-amino)-propyl ester in 5 ml methanol. The reaction mixture is stirred at RT for about 15 h and then substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. This gives 0.29 g of the title compound as a solid foam. M. p. 104-112° C. (unsharp)

Optical rotation: $[\alpha]_D^{20}=-65.3°$ (c=100 mg/ml, methanol)
MS: calc.: $C_{29} H_{39} N_3 O_4$ (493.65) fnd.: [M+1] 494.2 HPLC[min] 9.71

12. 4-((4aR,10bS)-9-Ethoxy-8-methoxy-2-methyl-1,2,3,4,4a,10b-hexahydro-benzo[c][1,6]naphthyridin-6-yl)-N-((R)-2-hydroxy-1-methyl-ethyl)-N-isopropyl-benzamide

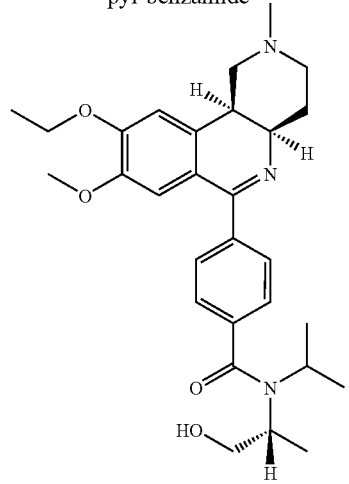

Prepared as described in example 11, starting from 4-Nitro-benzoic acid (R)-2-({1-[4-((4aR,10bS)-9-ethoxy-8-methoxy-2-methyl-1,2,3,4,4a,10b-hexahydro-benzo[c][1,6] naphthyridin-6-yl)-phenyl]-methanoyl}-isopropyl-amino)-propyl ester. M. p. 92.6-98° C. (unsharp, solid foam)

Optical rotation: $[\alpha]_D^{20}=-67.9°$ (c=100 mg/ml, methanol)
MS: calc.: $C_{29} H_{39} N_3 O_4$ (493.65) fnd.: [M+1] 494.2 HPLC[min] 9.82

13. 4-((4aR,10bS)-9-Ethoxy-8-methoxy-2-methyl-1,2,3,4,4a,10b-hexahydro-benzo[c][1,6]naphthyridin-6-yl)-N-(S)-2-hydroxy-1-methyl-ethyl)-N-isopropyl-benzamide (S)-2-hydroxy-hydrogen-succinate

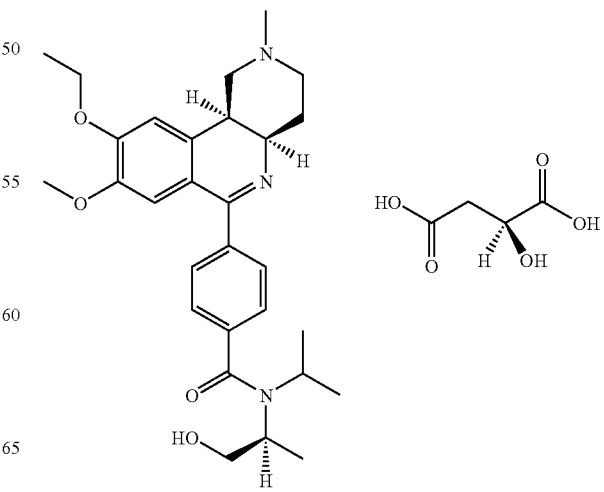

A solution of 1 equivalent of compound 11 in methanol is added to a solution of 1 equivalent of (S)-2-hydroxy-succinic acid in methanol; the salt solution is evaporated to dryness and the resulting solid is dried in vacuo. M. p. 75-80° C. (unsharp)

14. 4-((4aR,10bS)-9-Ethoxy-8-methoxy-2-methyl-1,2,3,4,4a,10b-hexahydro-benzo[c][1,6]-naphthyridin-6-yl)-N-((S)-2-hydroxy-1-methyl-ethyl)-N-isopropyl-benzamide (2R,3R)-hydrogen tartrate

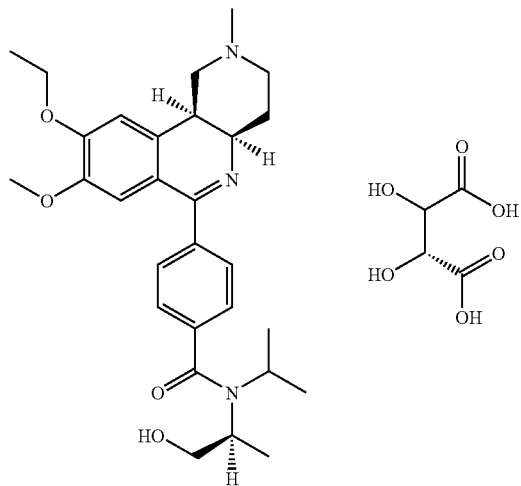

A solution of 1 equivalent of compound 11 in methanol is added to a solution of 1 equivalent of (2R,3R)-tartaric acid in methanol; the salt solution is evaporated to dryness and the resulting solid is dried in vacuo. M. p. 160-162° C.

Determination of HPLC-Values:

A Luna C18 (2) 150×2 mm column, packed with 5 μm particles from Phenomenex was used; the chromatography was carried out at room temperature using a flow of 0.4 ml/min. The solvent system employed was solvent A (water containing 5 mM ammonium acetate and 0.2% concentrated formic acid) and solvent B (90% acetonitrile and 10% Water containing 5 mM ammonium acetate and 0.2% concentrated formic acid), with the following gradient course being used:

| min   | % A | % B |
|-------|-----|-----|
| 0.00  | 98  | 2   |
| 4.00  | 98  | 2   |
| 14.00 | 40  | 60  |
| 14.01 | 0   | 100 |
| 16.00 | 0   | 100 |
| 16.01 | 98  | 2   |
| 18.00 | 98  | 2   |

The HPLC system was coupled online to a mass spectrometer as detection system. Detection was carried out by ESI-MS (Electrospray Ionisation—Mass Spectrometry) in the positive ionisation mode.

Under these HPLC conditions the Example 11 and Example 12 were chromatographically separated at 60% valley with retention times of 9.71 min and 9.82 min, respectively.

Starting Materials

A. 4-((4aR,10bS)-9-Ethoxy-8-methoxy-2-methyl-1,2,3,4,4a,10b-hexahydrobenzo[c][1,6]naphthyridin-6-yl)benzoic acid chloride dihydrochloride=4-((−)-cis-9-Ethoxy-8-methoxy-2-methyl-1,2,3,4,4a,10b-hexahydrobenzo[c][1,6]naphthyridin-6-yl)benzoic acid chloride dihydrochloride The title compound is obtained from 4-((4aR,10bS-9-ethoxy-8-methoxy-2-methyl-1,2,3,4,4a,10b-hexahydro-benzo[c][1,6]naphthyridin-6-yl)benzoic acid by the reaction, known to the person skilled in the art, with a chlorinating agent, such as thionyl chloride, oxalyl chloride, phosphorus trichloride or phosphorus pentachloride. The resulting acid chloride is directly used for the further reaction without purification.

B. 4-((4aR,10bS-9-Ethoxy-8-methoxy-2-methyl-1,2,3,4,4a,10b-hexahydrobenzo[c][1,6]naphthyridin-6-yl)benzoic acid=4-((−)-cis-9-Ethoxy-8-methoxy-2-methyl-1,2,3,4,4a,10b-hexahydrobenzo[c][1,6]naphthyridin-6-yl)benzoic acid The title compound is prepared as described in WO98/21208;

Optical rotation: $[\alpha]_D^{20}$=−109.7° (c=1, methanol+1.0 equivalent 0.1 N aq. sodium hydroxide)

C. Phenyl-acetic acid (S)-2-isopropylamino-propyl ester hydrochloride

To a suspension of 10 g of (S)-2-isopropylamino-propan-1-ol hydrochloride in 300 ml of dichloromethane 10 ml of phenyl-acetic acid chloride are added. The reaction mixture is stirred at RT for about 15 h and then substantially concentrated under reduced pressure, and the highly viscous residue is partitioned between dichloromethane and saturated sodium bicarbonate solution. The organic phase is washed with water, dried over sodium sulfate and concentrated. The resin-like residue is purified by silica gel chromatography, and the product fraction is separated off and concentrated. The residue is dissolved in 150 ml of 2-propanol and 25 ml 2 N HCl in water are added. The mixture is stirred for about 15 h and the resulting crystals are filtered off. This gives 10.9 g of the title compound. M. p. 114-118° C. (unsharp)

MS: calc.: $C_{14} H_{21} N O_2$ (235.33) fnd.: [M+1] 236.2

Analogously to starting material C, the following title compounds are obtained when the respective appropriately substituted acid chlorides and the appropriately substituted amino alkohols are used as reaction partners:

D. Benzoic acid (S)-2-isopropylamino-propyl ester

MS: calc.: $C_{13} H_{19} N O_2$ (221.30) fnd.: [M+1] 221.9

E. 3,4-Dimethoxy-benzoic acid (S)-2-isopropylamino-propyl ester

MS: calc.: $C_{15} H_{23} N O_4$ (282.35) fnd.: [M+1] 281.9

F. 3,5-Dimethoxy-benzoic acid (S)-2-isopropylamino-propyl ester

MS: calc.: $C_{15} H_{23} N O_4$ (282.35) fnd.: [M+1] 282

G. Acetic acid (S)-2-isopropylamino-propyl ester

MS: calc.: $C_8H_{17}NO_2$ (159.23) fnd.: [M+1] 159.9

H. Rac-Benzoic acid 3-isopropylamino-butyl ester

MS: calc.: $C_{14}H_{21}NO_2$ (235.33) fnd.: [M+1] 236.2

J. Rac-Phenyl-acetic acid 3-isopropylamino-butyl ester

MS: calc.: $C_{15}H_{23}NO_2$ (249.36) fnd.: [M+1] 250

K. Rac-(3,4-Dimethoxy-phenyl)-acetic acid 3-isopropylamino-butyl ester

MS: calc.: $C_{17}H_{27}NO_4$ (309.41) fnd.: [M+1] 310.2

L. 4-Nitro-benzoic acid (S)-2-isopropylamino-propyl ester

MS: calc.: $C_{13}H_{18}N_2O_4$ (266.30) fnd.: [M+1] 266.9

M. 4-Nitro-benzoic acid (R)-2-isopropylamino-propyl ester

MS: calc.: $C_{13}H_{18}N_2O_4$ (266.30) fnd.: [M+1] 266.9

The appropriately substituted amino alkohols are known from Tetrahedron Vol. 45, No. 16, pp. 4969 to 4988, 1989 or can be prepared analogously to the methods described there.

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating action and cilia-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumour necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherence proteins (e.g. integrins). The compounds according to the invention have smooth muscle-relaxant action, e.g. in the region of the bronchial system, of the blood circulation, and of the efferent urinary passages. Furthermore, they have cilia frequency-increasing action, for example in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) respiratory disorders of various origins (bronchitis, allergic bronchitis, bronchial asthma, emphysema, COPD); disorders associated with impaired cilia function or increased demands on ciliar clearance (bronchitis, mucoviscidosis), dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origins such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as anti-thrombotic, platelet aggregation-inhibiting substances.

The invention further relates to a method for the treatment of mammals including humans who are suffering from one of the abovementioned diseases. The method comprises administering a therapeutically effective and pharmacologically acceptable amount of one or more of the compounds according to the invention to the sick mammal.

The invention further relates to the compounds according to the invention for use in the treatment and/or prophylaxis of diseases, in particular the diseases mentioned.

The invention also relates to the use of the compounds according to the invention for the production of pharmaceutical compositions which are employed for the treatment and/or prophylaxis of the diseases mentioned.

The invention furthermore relates to pharmaceutical compositions for the treatment and/or prophylaxis of the diseases mentioned and which contain one or more of the compounds according to the invention.

A further subject of the invention is a commercial product, consisting of a customary secondary pack, a primary pack containing the pharmaceutical composition (for example an ampoule or a blister pack) and, if desired, an information leaflet, the pharmaceutical composition exhibiting antagonistic action against cyclic nucleotide phosphodiesterases of types 3 and 4 and leading to the attenuation of the symptoms of illnesses which are connected with cyclic nucleotide phosphodiesterases of types 3 and 4, and the suitability of the pharmaceutical composition for the prophylaxis or treatment of illnesses which are connected with cyclic nucleotide phosphodiesterases of types 3 and 4 being indicated on the secondary pack and/or on the information leaflet of the commercial product, and the pharmaceutical composition containing one or more compounds of formula 1 according to the invention. The secondary pack, the primary pack containing the pharmaceutical composition and the information leaflet otherwise comply with what would be regarded as standard to the person skilled in the art for pharmaceutical compositions of this type.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta-mimetics. In combination, on account of their cAMP degradation-inhibiting action, they in this case display a synergistic, superadditive activity. This comes to bear, for example, in their use in combination with PGE2 for the treatment of pulmonary hypertension.

The pharmaceutical compositions are prepared by processes which are known per se and familiar to the person skilled in the art As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1-99%. The dose for administration by inhalation is customarily between 0.1 and 3 mg per day. The customary dose in the case of systemic therapy (p.o. or i.v.) is between 0.01 and 10 mg per kilogram per day.

Biological Investigations

The second messenger cyclic AMP (CAMP) is known for inhibiting inflammatory cells and cells responsible for the immunological response. The PDE4-isoenzyme is widely distributed in cells associated with the initiation and spreading of inflammatory diseases (H Tenor and C Schudt, in "Phosphodiesterase Inhibitors", 21-40, "The Handbook of Immunopharmacology", Academic Press 1996); its inhibition results in the increase of the intracellular cyclic AMP concentration and thus in the inhibition of cellular activation (J E Souness et al., Immunopharmacology 47: 127-162, 2000).

The anti-inflammatory potential of PDE4 inhibitors in vivo has been described in various animal models (MMTeixeira, TIPS 18: 164-170, 1997). To examine the PDE4 inhibition on a cellular level (in vitro), a large number of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor alpha (TNFα) in monocytes, macrophages or dendritic cells (Gantner et al., Brit J Pharmacol 121: 221-231, 1997 and Pulmonary Pharmacol Therap 12: 377-386, 1999). The immunomodulatory potential of the PDE4 inhibitors furthermore becomes apparent by inhibition of T-cell responses such as cytokine synthesis or proliferation (D M Essayan, Biochem Pharmacol 57: 965-973, 1999). PDE4 inhibition by the substances according to the invention is thus a central indicator of the suppression of inflammatory processes.

Some of the cells involved in inflammatory processes contain, in addition to PDE4, also the PDE3 isoenzyme which likewise contributes to the total CAMP metabolism of these cells. Examples are endothelial cells, mast cells, T-cells, macrophages and dendritic cells. In these cell types, the inhibitory action of PDE4 inhibitors can be enhanced by additional PDE3 inhibition. In the case of (respiratory) smooth muscle cells, inhibition of the PDE3 activity is furthermore important for (broncho)relaxation (A Hatzelmann et al., in "Phosphodiesterase Inhibitors", 147-160, "The Handbook of ImmunoPharmacology", Academic Press, 1996).

A. Methodology

1. Inhibition of PDE Isoenzymes

The PDE activity was determined according to Thompson et al. (Adv Cycl Nucl Res 10: 69-92, 1979) with some modifications (Bauer and Schwabe, Naunyn-Schmiedeberg's Arch Pharmacol 311: 193-198, 1980). The test samples contained 20 mM Tris (pH 7.4), 5 mM $MgCl_2$, 0.5 µM cAMP or cGMP, [$^3$H]cAMP or [$^3$H]cGMP (about 30 000 cpm/sample), the PDE isoenzyme-specific additives described in greater detail below, the indicated concentrations of inhibitor and an aliquot of the enzyme solution in a total sample volume of 200 µl. Dilution series of the compounds according to the invention were prepared in DMSO and further diluted in the samples [1:100 (v/v)], to give the desired end concentration of the inhibitors at a DMSO concentration of 1% (v/v), which for its part has only a minute effect on PDE activity.

After preincubation at 37° C. for 5 minutes, the reaction was started by addition of the substrate (cAMP or cGMP). The samples were incubated at 37° C. for a further 15 min. The reaction was terminated by addition of 50 µl 0.2 N HCl. After cooling on ice for 10 minutes and addition of 25 µg 5'-nucleotidase (snake venom from Crotalus atrox), the mixture was again incubated at 37° C. for 10 min and the samples were then applied to QAE Sephadex A-25 columns (sample volume 1 ml). The columns were eluted with 2 ml of 30 mM ammonium formate (pH 6.0). The radioactivity of the eluate was measured and corrected by the corresponding blank values (measured in the presence of denatured protein); the blank values were less than 5% of the total radioactivity. In no case did the proportion of hydrolyzed nucleotide exceed 30% of the original substrate concentration.

PDE3 (cGMP-inhibited) was investigated in homogenates of human platelets (see Schudt et al., Biochem Pharmacol 1991: 42, 153-162) using cAMP or cGMP as substrate.

PDE4 (cAMP-specific) was investigated in the cytosol of human polymorphonuclear leukocytes (PMNL) [isolated from leukocyte concentrates, see Schudt et al., Arch Pharmacol 1991: 344, 682-690] using cAMP as substrate. The PDE3 inhibitor motapizone (1 µM) was used to suppress the PDE3 activity emanating from contaminated platelets.

The $IC_{50}$ values were determined from the concentration-inhibition curves by nonlinear regression.

B. Results

In the table below, the inhibitory concentrations according to section A1 [inhibitory concentrations as —log $IC_{50}$ (mol/l)] are indicated for a number of compounds according to the invention for the PDE4 and the PDE3 isoenzyme. The number of the compounds corresponds to the numbers of the examples in the section End products.

TABLE 1

| Compound | PDE4 | PDE3 |
|---|---|---|
| | [−log $IC_{50}$, mol/l] | |
| 1 | 9.8 | 7.3 |
| 2 | 9 | 7.6 |
| 3 | 9.4 | 7.5 |
| 4 | 9.3 | 7.4 |
| 5 | 9.2 | 7.1 |
| 6 | 9.2 | 7 |
| 7 | 9.6 | 7.5 |
| 8 | 9.6 | 7.3 |
| 11 | 8.9 | 7.1 |
| 12 | 8.8 | 7.1 |

The invention claimed is:

1. A compound of formula 1,

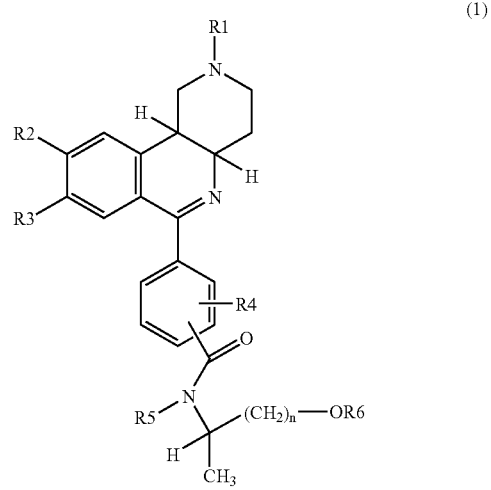

in which

R1 is methyl,

R2 is 1-4C-alkoxy,

R3 is 1-4C-alkoxy,

R4 is hydrogen,

R5 is 1-4C-alkyl,

R6 is hydrogen, 1-4C-alkylcarbonyl, Arylcarbonyl or Aryl-1-2C-alkylcarbonyl,

Aryl is phenyl or phenyl substituted by R7 and/or R8,

R7 is nitro, 1-2C-alkyl or 1-2C-alkoxy,

R8 is 1-2C-alkoxy, n is 1 or 2, or a salt, thereof.

2. A compound of formula 1 as claimed in claim 1, in which

R1 is methyl,

R2 is methoxy or ethoxy,

R3 is methoxy,

R4 is hydrogen,

R5 is isopropyl, and in which either

R6 is hydrogen, phenylcarbonyl, benzylcarbonyl, 4-nitrophenylcarbonyl, 3-4-dimethoxyphenylcarbonyl, 3-5-dimethoxyphenylcarbonyl or acetyl and
n is 1,
or
R6 is phenylcarbonyl, benzylcarbonyl or 3,4-dimethoxybenzylcarbonyl and
n is 2,
or a salt thereof.

3. A compound of formula 1 as claimed in claim 1, in which
R1 is methyl,
R2 is methoxy or ethoxy,
R3 is methoxy,
R4 is hydrogen,
R5 is isopropyl,
and in which either
R6 is hydrogen, benzylcarbonyl, 4-nitrophenylcarbonyl, 3,4-dimethoxyphenylcarbonyl, 3,5-dimethoxyphenylcarbonyl or acetyl and
n is 1,
or
R6 is phenylcarbonyl, benzylcarbonyl or 3,4-dimethoxybenzylcarbonyl and
n is 2,
or a salt thereof.

4. A compound of formula 1 as claimed in claim 1 selected from the group consisting of
Phenyl-acetic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester,
Benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester,
3,4-Dimethoxy-benzoic acid (S)-2-({1-[4-((4aR,10bS)-9-ethoxy-8-methoxy-2-methyl-1,2,3,4,4a,10b-hexahydro-benzo[c][1,6]-naphthyridin-6-yl)-phenyl]-methanoyl}-isopropyl-amino)-propyl ester,
3,5-Dimethoxy-benzoic acid (S)-2-({1-[4-((4aR,10bS)-9-ethoxy-8-methoxy-2-methyl-1,2,3,4,4a,10b-hexahydro-benzo[c][1,6]-naphthyridin-6-yl)-phenyl]-methanoyl}-isopropyl-amino)-propyl ester,
Acetic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester,
Benzoic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester,
Phenyl-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester,
(3,4-Dimethoxy-phenyl)-acetic acid 3-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-butyl ester,
4-Nitro-benzoic acid (S)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino-propyl ester,
4-Nitro-benzoic acid (R)-2-({1-[4-((4aR,10bS)-9-ethoxy-8-methoxy-2-methyl-1,2,3,4,4a,10b-hexahydro-benzo[c][1,6]naphthyridin-6-yl)-phenyl]-methanoyl}-isopropyl-amino)-propyl ester,
4-((4aR,10bS)-9-Ethoxy-8-methoxy-2-methyl-1,2,3,4,4a,10b-hexahydro-benzo[c][1,6]naphthyridin-6-yl)-N-((S)-2-hydroxy-1-methyl-ethyl-N-isopropyl-benzamide,
4-((4aR,10bS)-9-Ethoxy-8-methoxy-2-methyl-1,2,3,4,4a,10b-hexahydro-benzo[c][1,6]naphthyridin-6-yl)-N-((R)-2-hydroxy-1-methyl-ethyl-N-isopropyl-benzamide,
and salts thereof.

5. A compound of formula 1 as claimed in claim 1, in which the hydrogen atoms in positions 4a and 10b are in the cis position relative to one another, or a salt thereof.

6. A compound of formula 1 as claimed in claim 1 which has with respect to the chiral centers the configuration shown in formulae (1*) or (1**):

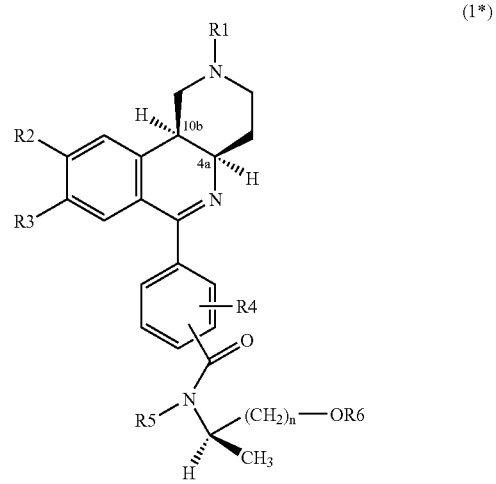

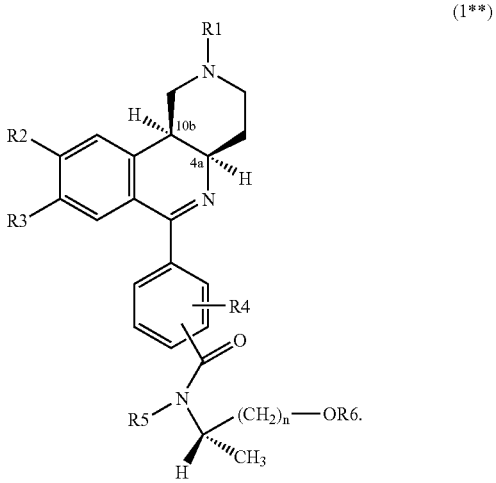

7. A pharmaceutical composition comprising one or more compounds of formula 1 as claimed in claim 1, or a pharmaceutically acceptable salt thereof, together with a pharmaceutically acceptable auxiliary and/or excipient.

* * * * *